(12) United States Patent
Naiki et al.

(10) Patent No.: US 9,365,533 B2
(45) Date of Patent: Jun. 14, 2016

(54) COUMARIN DERIVATIVE

(71) Applicant: NIPPON ZOKI PHARMACEUTICAL CO., LTD., Osaka-shi, Osaka (JP)

(72) Inventors: Mitsuru Naiki, Kato (JP); Tomoyuki Okada, Kato (JP); Kazuyoshi Sawada, Kato (JP); Takashi Ogino, Kato (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/429,300

(22) PCT Filed: Sep. 20, 2013

(86) PCT No.: PCT/JP2013/075414
§ 371 (c)(1),
(2) Date: Mar. 18, 2015

(87) PCT Pub. No.: WO2014/046224
PCT Pub. Date: Mar. 27, 2014

(65) Prior Publication Data
US 2015/0232440 A1   Aug. 20, 2015

(30) Foreign Application Priority Data
Sep. 21, 2012 (JP) ................... 2012-208656

(51) Int. Cl.
*C07D 311/02* (2006.01)
*C07D 311/12* (2006.01)

(52) U.S. Cl.
CPC .................... *C07D 311/12* (2013.01)

(58) Field of Classification Search
CPC ..................................... C07D 311/18
USPC ........................................ 549/288
See application file for complete search history.

(56) References Cited

U.S. PATENT DOCUMENTS

| | | | |
|---|---|---|---|
| 5,922,755 | A | 7/1999 | Tanaka et al. |
| 6,166,068 | A | 12/2000 | Tanaka et al. |
| 6,191,164 | B1 | 2/2001 | Lang et al. |
| 2008/0020068 | A1 | 1/2008 | Germer et al. |
| 2011/0009398 | A1 | 1/2011 | Sakai et al. |

FOREIGN PATENT DOCUMENTS

| | | |
|---|---|---|
| JP | H10-67772 A | 3/1998 |
| JP | 2008-505064 A | 2/2008 |
| WO | 94/23714 A1 | 10/1994 |
| WO | 2009/014100 A1 | 1/2009 |

OTHER PUBLICATIONS

West (Solid-State Chemistry and Its Applications, 1984, John Wiley & Sons).*
Dec. 17, 2013 Search Report issued in International Application No. PCT/JP2013/075414.
Patonay et al; "Synthesis, Antibacterial and Antifungal Activity of 4-Hydroxycoumarin Derivatives Analogs of Novobiocin;" Die Pharmazie; 1984; vol. 39; No. 2; pp. 86-91; compunds 11-13.
"Preparation of Some New Sulphanilamido Coumarins;" Science and Culture; 1965; vol. 31; No. 1; p. 27.
"Synthesis of Some Biochemically Important Derivatives of 3-amino Coumarins;" Science and Culture; 1971; vol. 37; No. 1; pp. 58-59.

* cited by examiner

*Primary Examiner* — Nizal Chandrakumar
(74) *Attorney, Agent, or Firm* — Oliff PLC

(57) ABSTRACT

A novel coumarin derivative or a pharmaceutically acceptable salt thereof and also to provide a pharmaceutical agent containing such a compound as an active ingredient is provided. The coumarin derivative or a pharmaceutically acceptable salt thereof exhibits an excellent suppressive action to the destruction of cartilage and suppressive action to the proliferation of synovial cells in a pharmacological test where the release of sulfated glycosaminoglycans (sGAG) and the proliferation of synovial cells are used as indicators whereby it is very useful as an active ingredient of a pharmaceutical composition such as a preventive or therapeutic agent for arthropathy such as osteoarthritis or chronic rheumatoid arthritis.

19 Claims, No Drawings

COUMARIN DERIVATIVE

TECHNICAL FIELD

The present invention relates to a novel coumarin derivative or a pharmaceutically acceptable salt thereof. The present invention also relates to a pharmaceutical agent such as a preventive or therapeutic agent for arthropathy containing at least one member of a novel coumarin derivative and a pharmaceutically acceptable salt thereof as an active ingredient.

BACKGROUND ART

Arthropathy is a joint disease induced by various diseases. Among various types of arthropathy, numbers of patients suffering from osteoarthritis (OA) and chronic rheumatoid arthritis (RA) are particularly large and those have been believed to be the main arthropathy. When degeneration and abrasion of cartilage are resulted in osteoarthritis due to some causes such as mechanical stimulation, they grow as abnormal cartilage and osteophyte on the surrounding site suffering from no burden during the repairing process whereupon deformation of a joint proceeds. As a result of such a change, synovial membrane in the joint is inflamed and abnormally grows whereupon water is accumulated in the joint. As to the osteoarthritis, osteoarthritis of knee and osteoarthritis of hip have been well known. Further, in chronic rheumatoid arthritis, non-specific inflammation is induced in synovial membrane in the joint resulting in pain and swelling accompanied by proliferation of synovial cells whereupon joint fluid increases and destruction of cartilage and bone proceeds. With regard to the therapy of osteoarthritis and chronic rheumatoid arthritis, mechanism of onset and progress thereof has not been completely clarified yet whereby radical therapy for eliminating the causes is unable to be expected at present and, in addition, no therapeutic method for regenerating the abraded cartilage and the deformed joint to the original state has been established yet. Accordingly, a conservative therapy by means of exercise therapy, physical therapy, pharmaceutical agent therapy, etc. for relieving the pain and the symptom and not for further worsening the state of disease is a fundamental means. In view of the current situations as mentioned above, there has been a strong demand from the clinical site for drugs exhibiting excellent effect to arthropathy such as osteoarthritis and chronic rheumatoid arthritis.

The present inventors have found that the coumarin derivative of the present invention is useful as a pharmaceutical agent such as a preventive or therapeutic agent for arthropathy since it exhibits a suppressive action for the destruction of cartilage and a suppressive action for the proliferation of synovial cells. With regard to a coumarin derivative, a compound where sulfonylamino is substituted at 3-position of a coumarin skeleton is disclosed in Non-Patent Documents 1 and 2 but those documents merely report that such a compound is synthesized and do not mention at all that the compound exhibits a pharmacological action.

PRIOR ART DOCUMENTS

Non-Patent Documents

Non-Patent Document 1: Science and Culture, Vol. 31, No. 1, page 27 (1965)
Non-Patent Document 2: Science and Culture, Vol. 37, No. 1, pages 58 to 59 (1971)

SUMMARY OF THE INVENTION

Problems to be Solved by the Invention

The purpose of the present invention is to provide a novel coumarin derivative or a pharmaceutically acceptable salt thereof and a pharmaceutical agent containing the same as an active ingredient and, more particularly, to provide a pharmaceutical agent which is able to be used as a preventive or therapeutic agent for arthropathy, etc. due to the fact the compound exhibits a pharmacological action such as suppression of the destruction of cartilage and suppression of the proliferation of synovial cells.

Means for Solving the Problems

The present inventors have eagerly conducted studies for solving the above purpose and, as a result, they have found that a coumarin derivative represented by the following formula (I) or a pharmaceutically acceptable salt thereof exhibits an excellent pharmacological action such as suppression of the destruction of cartilage or suppression of the proliferation of synovial cells and is useful as a pharmaceutical agent such as a preventive or therapeutic agent for arthropathy whereupon they have accomplished the present invention.

Advantages of the Invention

Since the coumarin derivative or a pharmaceutical salt thereof according to the present invention exhibits an excellent suppressive action in the pharmacological test where the release of sulphated glycosaminoglycans (sGAG) and the proliferation of synovial cells are indicators, it is highly useful as a pharmaceutical agent such as a preventive or therapeutic agent for arthropathy such as osteoarthritis or chronic rheumatoid arthritis.

MODE FOR CARRYING OUT THE INVENTION

The present invention relates to a coumarin derivative represented by the following formula (I) or a pharmaceutically acceptable salt thereof useful as a preventive or therapeutic agent for arthropathy, etc.

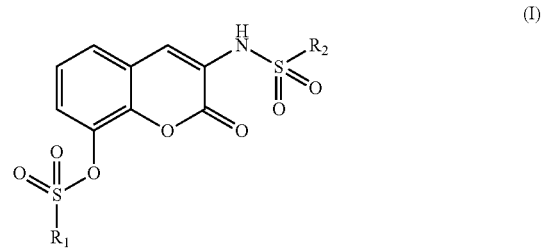

(I)

[In the formula, $R_1$ and $R_2$ are the same or different, and are (a) phenyl optionally substituted with alkoxy, alkyl, cyano, nitro, hydroxy, trifluoromethyl, amino, carboxy, alkoxycarbonyl, phenyl or one or two halogen(s), (b) pyridyl, (c) alkyl or (d) thienyl.]

In the substituent of the above formula (I), the alkyl is preferably a linear or branched alkyl having 1 to 4 carbon(s) such as methyl, ethyl, propyl, isopropyl, butyl, isobutyl, sec-butyl or t-butyl.

The alkoxy is preferably a linear or branched alkoxy having 1 to 4 carbon(s) such as methoxy, ethoxy, n-propoxy, isopropoxy, n-butoxy, isobutoxy, sec-butoxy or t-butoxy.

The halogen is fluorine, chlorine, bromine, iodine or the like.

As hereunder, general method for producing the compound of the present invention is shown. However, in producing a specific compound, it is a matter of course that persons skilled in the art are able to appropriately modify the method depending upon the chemical structure thereof.

A compound of the formula (I) is able to be produced by a sulfonylamidation reaction of a compound of the formula (II). For example, the sulfonylamidation reaction may be conducted for the compound of the formula (II) and a substituted benzenesulfonyl halide in pyridine or a basic solvent at an appropriate temperature between room temperature and boiling point of the solvent.

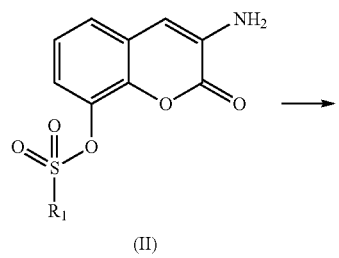

(II)

A compound of the formula (II) is prepared by an acid hydrolysis reaction of a compound of the formula (III). For example, the acid hydrolysis reaction can be conducted in a mixed solvent of an organic acid such as acetic acid with sulfuric acid adjusted to an appropriate concentration at an appropriate temperature preferably from room temperature to boiling point of the solvent.

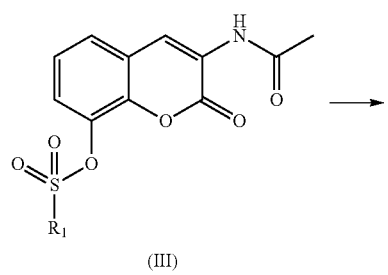

(III)

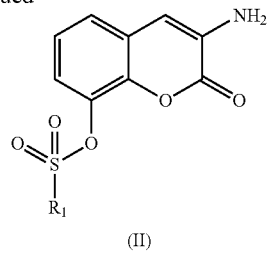

(II)

A compound of the formula (III) is prepared by a sulfonyl esterification reaction of a compound (IV) of the formula (IV). For example, the sulfonyl esterification reaction can be conducted using a compound of the formula (IV) and a substituted benzenesulfonyl halide in a basic solvent such as pyridine at advantageous temperature preferably from room temperature to boiling point of the solvent.

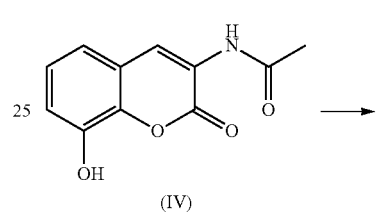

(IV)

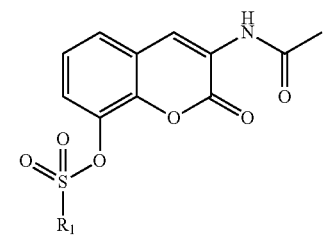

(III)

When $R_1$ and $R_2$ are the same substituent in a compound represented by the formula (I), 3-amino-2-oxo-8-hydroxychromene is subjected to a sulfonylamidation reaction and a sulfonyl esterification reaction at the same time as shown in the following Example 2 whereupon a coumarin derivative of the present invention can be produced.

A compound represented by the above formula (I) includes various salts thereof when such pharmaceutically acceptable salts are available and examples thereof include an addition salt with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; a salt with alkali metal such as sodium or potassium, with alkali earth metal such as calcium or magnesium or with metal such as aluminum; and a salt with a base such as ammonia or an organic amine. The salts as such may be produced from each free compound by a known method or may be converted each other. Moreover, when the coumarin derivative of the present invention is present in a form of a stereoisomer such as cis-trans isomer, optical isomer or structural isomer, a solvate such as hydrate or a metal complex compound, it also covers any of the stereoisomer, solvate and complex compound thereof.

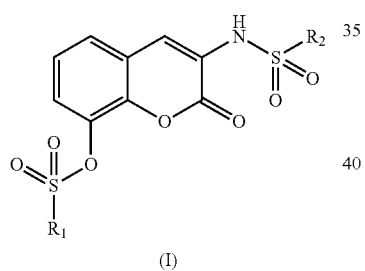

(I)

Examples of the compound produced as such are shown as follows. Further, substituents corresponding to $R^1$ and $R^2$ of the above formula (I) in each compound are shown in Tables 1 and 2. With regard to the substituents $R_1$ and $R_2$ in the tables, methyl, ethyl, phenyl, pyridyl and thienyl are represented by Me, Et, Ph, Py and thienyl, respectively and, with regard to others, they are expressed using symbols of elements. Hereinafter, in referring to each compound, each of the following compound Nos. is used.

3-[(4-Methoxyphenyl)sulfonylamino]-2-oxochromen-8-yl 4-methoxybenzenesulfonate [Compound 1]
3-[(3-Methoxyphenyl)sulfonylamino]-2-oxochromen-8-yl 3-methoxybenzenesulfonate [Compound 2]
3-[(2-Methoxyphenyl)sulfonylamino]-2-oxochromen-8-yl 2-methoxybenzenesulfonate [Compound 3]
2-Oxo-3-(p-tolylsulfonylamino)chromen-8-yl 4-methylbenzenesulfonate [Compound 4]
3-(m-Tolylsulfonylamino)-2-oxochromen-8-yl 3-methylbenzenesulfonate [Compound 5]
3-(o-Tolylsulfonylamino)-2-oxochromen-8-yl 2-methylbenzenesulfonate [Compound 6]
3-[(4-Chlorophenyl)sulfonylamino]-2-oxochromen-8-yl 4-chlorobenzenesulfonate [Compound 7]
3-[(3-Chlorophenyl)sulfonylamino]-2-oxochromen-8-yl 3-chlorobenzenesulfonate [Compound 8]
3-[(2-Chlorophenyl)sulfonylamino]-2-oxochromen-8-yl 2-chlorobenzenesulfonate [Compound 9]
3-[(4-Fluorophenyl)sulfonylamino]-2-oxochromen-8-yl 4-fluorobenzenesulfonate [Compound 10]
3-[(3-Fluorophenyl)sulfonylamino]-2-oxochromen-8-yl 3-fluorobenzenesulfonate [Compound 11]
3-[(2-Fluorophenyl)sulfonylamino]-2-oxochromen-8-yl 2-fluorobenzenesulfonate [Compound 12]
3-[(4-Cyanophenyl)sulfonylamino]-2-oxochromen-8-yl 4-cyanobenzenesulfonate [Compound 13]
3-[(3-Cyanophenyl) sulfonylamino]-2-oxochromen-8-yl 3-cyanobenzenesulfonate [Compound 14]
3-[(2-Cyanophenyl)sulfonylamino]-2-oxochromen-8-yl 2-cyanobenzenesulfonate [Compound 15]
3-[(4-Nitrophenyl)sulfonylamino]-2-oxochromen-8-yl 4-nitrobenzenesulfonate [Compound 16]
3-[(3-Nitrophenyl)sulfonylamino]-2-oxochromen-8-yl 3-nitrobenzenesulfonate [Compound 17]
3-[(2-Nitrophenyl)sulfonylamino]-2-oxochromen-8-yl 2-nitrobenzenesulfonate [Compound 18]
3-[(4-Hydroxyphenyl)sulfonylamino]-2-oxochromen-8-yl 4-hydroxybenzenesulfonate [Compound 19]
3-(Benzenesulfonylamino)-2-oxochromen-8-yl 4-cyanobenzenesulfonate [Compound 20]
3-[(4-Cyanophenyl)sulfonylamino]-2-oxochromen-8-yl benzenesulfonate [Compound 21]
3-[(3-Cyanophenyl)sulfonylamino]-2-oxochromen-8-yl benzenesulfonate [Compound 22]
3-[(4-Nitrophenyl)sulfonylamino]-2-oxochromen-8-yl benzenesulfonate [Compound 23]
3-[(3-Nitrophenyl)sulfonylamino]-2-oxochromen-8-yl benzenesulfonate [Compound 24]
3-[(3-Fluorophenyl)sulfonylamino]-2-oxochromen-8-yl benzenesulfonate [Compound 25]
3-[(3,4-Difluorophenyl)sulfonylamino]-2-oxochromen-8-yl benzenesulfonate [Compound 26]
2-Oxo-3-[[4-(trifluoromethyl)phenyl]sulfonylamino]-chromen-8-yl benzenesulfonate [Compound 27]
2-Oxo-3-[[3-(trifluoromethyl)phenyl]sulfonylamino]-chromen-8-yl benzenesulfonate [Compound 28]
3-[(4-Chlorophenyl)sulfonylamino]-2-oxochromen-8-yl benzenesulfonate [Compound 29]
2-Oxo-3-[(4-phenylphenyl)sulfonylamino]chromen-8-yl benzenesulfonate [Compound 30]
3-[(3-Bromophenyl)sulfonylamino]-2-oxochromen-8-yl benzenesulfonate [Compound 31]
3-[(3-Bromophenyl)sulfonylamino]-2-oxochromen-8-yl 3-bromobenzenesulfonate [Compound 32]
2-Oxo-3-[[3-(trifluoromethyl)phenyl]sulfonylamino]-chromen-8-yl 3-(trifluoromethyl)benzenesulfonate [Compound 33]
3-(Benzenesulfonamide)-2-oxochromen-8-yl 3-bromobenzenesulfonate [Compound 34]
3-(Benzenesulfonamide)-2-oxochromen-8-yl 3-(trifluoromethyl)benzenesulfonate [Compound 35]
3-[(3-Bromophenyl)sulfonylamino)]-2-oxochromen-8-yl pyridine-3-sulfonate [Compound 36]
3-[(3-Bromophenyl)sulfonylamino)]-2-oxochromen-8-yl methanesulfonate [Compound 37]
2-Oxo-3-(3-pyridylsulfonylamino)chromen-8-yl 3-bromobenzenesulfonate [Compound 38]
3-(Methanesulfonamide)-2-oxochromen-8-yl 3-bromobenzenesulfonate [Compound 39]
3-(Methanesulfonamide)-2-oxochromen-8-yl benzene-sulfonate [Compound 40]
2-Oxo-3-[[3-(trifluoromethyl)phenyl]sulfonylamino]-chromen-8-yl 4-nitrobenzenesulfonate [Compound 41]
3-[(4-Nitrophenyl)sulfonylamino]-2-oxochromen-8-yl 3-(trifluoromethyl)benzenesulfonate [Compound 42]
3-[(3-Nitrophenyl)sulfonylamino]-2-oxochromen-8-yl thiophene-2-sulfonate [Compound 43]
2-Oxo-3-(2-thienylsulfonylamino)chromen-8-yl 3-nitrobenzenesulfonate [Compound 44]
4-[[8-(3-Nitrophenyl)sulfonyloxy-2-oxochromen-3-yl-sulfamoyl]benzoic acid [Compound 45]
2-Oxo-3-[[3-(trifluoromethyl)phenyl]sulfonylamino]-chromen-8-yl 4-aminobenzenesulfonate hydrochloride [Compound 46]
3-[(4-Aminophenyl)sulfonylamino]-2-oxochromen-8-yl 3-(trifluoromethyl)benzenesulfonate [Compound 47]
Ethyl 4-[3-[(3-nitrophenyl)sulfonylamino]-2-oxochromen-8-yl]oxysulfonylbenzoate [Compound 48]
4-[3-[(3-Nitrophenyl)sulfonylamino]-2-oxochromen-8-yl] oxysulfonylbenzoic acid [Compound 49]
2-Oxo-3-[[3-(trifluoromethyl)phenyl]sulfonylamino]-chromen-8-yl 3-nitrobenzenesulfonate [Compound 50]
3-[(3-(Nitrophenyl)sulfonylamino]-2-oxochromen-8-yl 3-(trifluoromethyl)benzenesulfonate [Compound 51]
2-Oxo-3-[(4-phenylphenyl)sulfonylamino]chromen-8-yl 3-(trifluoromethyl)benzenesulfonate [Compound 52]
2-Oxo-3-[(4-phenylphenyl)sulfonylamino]chromen-8-yl 3-bromobenzenesulfonate [Compound 53]
3-[(3-Bromophenyl)sulfonylamino]-2-oxochromen-8-yl 3-nitrobenzenesulfonate [Compound 54]
2-Oxo-3-[(4-phenylphenyl)sulfonylamino]chromen-8-yl 3-nitrobenzenesulfonate [Compound 55]
3-[(3-Bromophenyl)sulfonylamino]-2-oxochromen-8-yl 3-(trifluoromethyl)benzenesulfonate [Compound 56]
2-Oxo-3-[[3-(trifluoromethyl)phenyl]sulfonylamino]-chromen-8-yl 4-(trifluoromethyl)benzenesulfonate [Compound 57]
3-[(3-Bromophenyl)sulfonylamino]-2-oxochromen-8-yl 4-(trifluoromethyl)benzenesulfonate [Compound 58]
3-[(3-Nitrophenyl)sulfonylamino]-2-oxochromen-8-yl 3-bromobenzenesulfonate [Compound 59]
2-Oxo-3-[[3-(trifluoromethyl)phenyl]sulfonylamino]-chromen-8-yl 3-bromobenzenesulfonate [Compound 60]
2-Oxo-3-[[4-(trifluoromethyl)phenyl]sulfonylamino]-chromen-8-yl 3-bromobenzenesulfonate [Compound 61]

3-[(3-Nitrophenyl)sulfonylamino]-2-oxochromen-8-yl 4-phenylbenzenesulfonate [Compound 62]
2-Oxo-3-[[3-(trifluoromethyl)phenyl]sulfonylamino]-chromen-8-yl 4-phenylbenzenesulfonate [Compound 63]
2-Oxo-3-[[4-(trifluoromethyl)phenyl]sulfonylamino]-chromen-8-yl 4-phenylbenzenesulfonate [Compound 64]
3-[(3-Bromophenyl)sulfonylamino]-2-oxochromen-8-yl 4-phenylbenzenesulfonate [Compound 65]
2-Oxo-3-[(4-phenylphenyl]sulfonylamino]chromen-8-yl 4-phenylbenzenesulfonate [Compound 66]
2-Oxo-3-[[4-(trifluoromethyl)phenyl]sulfonylamino]-chromen-8-yl 3-nitrobenzenesulfonate [Compound 67]
2-Oxo-3-[[4-(trifluoromethyl)phenyl]sulfonylamino]-chromen-8-yl 3-(trifluoromethyl)benzenesulfonate [Compound 68]
3-[(3-Nitrophenyl)sulfonylamino]-2-oxochromen-8-yl 4-(trifluoromethyl)benzenesulfonate [Compound 69]
2-Oxo-3-[(4-phenylphenyl)sulfonylamino]chromen-8-yl 4-(trifluoromethyl)benzenesulfonate [Compound 70]

TABLE 1

| Compound No. | $R_1$ | $R_2$ |
| --- | --- | --- |
| 1 | 4-OMePh | 4-OMePh |
| 2 | 3-OMePh | 3-OMePh |
| 3 | 2-OMePh | 2-OMePh |
| 4 | 4-MePh | 4-MePh |
| 5 | 3-MePh | 3-MePh |
| 6 | 2-MePh | 2-MePh |
| 7 | 4-ClPh | 4-ClPh |
| 8 | 3-ClPh | 3-ClPh |
| 9 | 2-ClPh | 2-ClPh |
| 10 | 4-FPh | 4-FPh |
| 11 | 3-FPh | 3-FPh |
| 12 | 2-FPh | 2-FPh |
| 13 | 4-CNPh | 4-CNPh |
| 14 | 3-CNPh | 3-CNPh |
| 15 | 2-CNPh | 2-CNPh |
| 16 | 4-$NO_2$Ph | 4-$NO_2$Ph |
| 17 | 3-$NO_2$Ph | 3-$NO_2$Ph |
| 18 | 2-$NO_2$Ph | 2-$NO_2$Ph |
| 19 | 4-OHPh | 4-OHPh |
| 20 | 4-CNPh | Ph |
| 21 | Ph | 4-CNPh |
| 22 | Ph | 3-CNPh |
| 23 | Ph | 4-$NO_2$Ph |
| 24 | Ph | 3-$NO_2$Ph |
| 25 | Ph | 3-FPh |
| 26 | Ph | 3,4-$F_2$Ph |
| 27 | Ph | 4-$CF_3$Ph |
| 28 | Ph | 3-$CF_3$Ph |
| 29 | Ph | 4-ClPh |
| 30 | Ph | 4-PhPh |
| 31 | Ph | 3-BrPh |
| 32 | 3-BrPh | 3-BrPh |
| 33 | 3-$CF_3$Ph | 3-$CF_3$Ph |
| 34 | 3-BrPh | Ph |
| 35 | 3-$CF_3$Ph | Ph |

TABLE 2

| Compound No. | $R_1$ | $R_2$ |
| --- | --- | --- |
| 36 | 3-Py | 3-BrPh |
| 37 | Me | 3-BrPh |
| 38 | 3-BrPh | 3-Py |
| 39 | 3-BrPh | Me |
| 40 | Ph | Me |
| 41 | 4-$NO_2$Ph | 3-$CF_3$Ph |
| 42 | 3-$CF_3$Ph | 4-$NO_2$Ph |
| 43 | 2-thienyl | 3-$NO_2$Ph |
| 44 | 3-$NO_2$Ph | 2-thienyl |

TABLE 2-continued

| Compound No. | $R_1$ | $R_2$ |
| --- | --- | --- |
| 45 | 3-$NO_2$Ph | 4-COOHPh |
| 46 | 4-$NH_2$Ph | 3-$CF_3$Ph |
| 47 | 3-$CF_3$Ph | 4-$NH_2$Ph |
| 48 | 4-COOEtPh | 3-$NO_2$Ph |
| 49 | 4-COOHPh | 3-$NO_2$Ph |
| 50 | 3-$NO_2$Ph | 3-$CF_3$Ph |
| 51 | 3-$CF_3$Ph | 3-$NO_2$Ph |
| 52 | 3-$CF_3$Ph | 4-PhPh |
| 53 | 3-BrPh | 4-PhPh |
| 54 | 3-$NO_2$Ph | 3-BrPh |
| 55 | 3-$NO_2$Ph | 4-PhPh |
| 56 | 3-$CF_3$Ph | 3-BrPh |
| 57 | 4-$CF_3$Ph | 3-$CF_3$Ph |
| 58 | 4-$CF_3$Ph | 3-BrPh |
| 59 | 3-BrPh | 3-$NO_2$Ph |
| 60 | 3-BrPh | 3-$CF_3$Ph |
| 61 | 3-BrPh | 4-$CF_3$Ph |
| 62 | 4-PhPh | 3-$NO_2$Ph |
| 63 | 4-PhPh | 3-$CF_3$Ph |
| 64 | 4-PhPh | 4-$CF_3$Ph |
| 65 | 4-PhPh | 3-BrPh |
| 66 | 4-PhPh | 4-PhPh |
| 67 | 3-$NO_2$Ph | 4-$CF_3$Ph |
| 68 | 3-$CF_3$Ph | 4-$CF_3$Ph |
| 69 | 4-$CF_3$Ph | 3-$NO_2$Ph |
| 70 | 4-$CF_3$Ph | 4-PhPh |

Preferred embodiments of the present invention will be shown as hereunder.

(1) A coumarin derivative represented by the above formula (I) or a pharmaceutically acceptable salt thereof.

(2) The coumarin derivative or a pharmaceutically acceptable salt thereof according to the above (1), wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

(3) The coumarin derivative or a pharmaceutically acceptable salt thereof according to the above (2), wherein $R_1$ and $R_2$ are the same or different, and are phenyl substituted with alkoxy, alkyl, cyano, nitro, hydroxy, trifluoromethyl, amino, carboxy, alkoxycarbonyl, phenyl or one or two halogen(s).

(4) The coumarin derivative or a pharmaceutically acceptable salt thereof according to the above (3), wherein one of $R_1$ and $R_2$ is phenyl substituted with trifluoromethyl.

(5) The coumarin derivative or a pharmaceutically acceptable salt thereof according to the above (4), wherein $R_1$ or $R_2$ which is not phenyl submitted with trifluoromethyl is phenyl substituted with trifluoromethyl or halogen.

(6) The coumarin derivative or a pharmaceutically acceptable salt thereof according to the above (5), wherein the halogen is bromine.

(7) A pharmaceutical agent containing at least one member of a coumarin derivative represented by the above formula (I) and a pharmaceutically acceptable salt thereof.

(8) The pharmaceutical agent according to the above (7), wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

(9) The pharmaceutical agent according to the above (8), wherein $R_1$ and $R_2$ are the same or different, and are phenyl substituted with alkoxy, alkyl, cyano, nitro, hydroxy, trifluoromethyl, amino, carboxy, alkoxycarbonyl, phenyl, or phenyl substituted with one or two halogen(s).

(10) The pharmaceutical agent according to the above (9), wherein one of $R_1$ and $R_2$ is phenyl substituted with trifluoromethyl.

(11) The pharmaceutical agent according to the above (10), wherein $R_1$ or $R_2$ which is not phenyl substituted with trifluoromethyl is phenyl substituted with trifluoromethyl or halogen.

(12) The pharmaceutical agent according to the above (11), wherein the halogen is bromine.

(13) The pharmaceutical agent according to any of the above (7) to (12), wherein the pharmaceutical agent is a preventive or therapeutic agent for arthropathy.

(14) The pharmaceutical agent according to the above (13), wherein the arthropathy is osteoarthritis.

(15) The pharmaceutical agent according to the above (13), wherein the arthropathy is chronic rheumatoid arthritis.

(16) The pharmaceutical agent according to any of the above (7) to (15), wherein the pharmaceutical agent is an oral agent.

(17) The pharmaceutical agent according to any of the above (7) to (15), wherein the pharmaceutical agent is an injection agent.

(18) The coumarin derivative represented by the above formula (I) or a pharmaceutically acceptable salt thereof for use in the prevention or the treatment of arthropathy.

(19) The coumarin derivative or a pharmaceutically acceptable salt thereof according to the above (18), wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

(20) The coumarin derivative or a pharmaceutically acceptable salt thereof according to the above (19), wherein $R_1$ and $R_2$ are the same or different, and are phenyl substituted with alkoxy, alkyl, cyano, nitro, hydroxy, trifluoromethyl, amino, carboxy, alkoxycarbonyl, phenyl or one or two halogen(s).

(21) The coumarin derivative or a pharmaceutically acceptable salt thereof according to the above (20), wherein one of $R_1$ and $R_2$ is phenyl substituted with trifluoromethyl.

(22) The coumarin derivative or a pharmaceutically acceptable salt thereof according to the above (21), wherein $R_1$ or $R_2$ which is not phenyl substituted with trifluoromethyl is phenyl substituted with trifluoromethyl or halogen.

(23) The coumarin derivative or a pharmaceutically acceptable salt thereof according to the above (22), wherein the halogen is bromine.

(24) The coumarin derivative or a pharmaceutically acceptable salt thereof according to any of the above (18) to (23), wherein the arthropathy is osteoarthritis.

(25) The coumarin derivative or a pharmaceutically acceptable salt thereof according to any of the above (18) to (23), wherein the arthropathy is chronic rheumatoid arthritis.

(26) A method for preventing or treating arthropathy, comprising administering an effective amount of at least one of the coumarin derivative represented by the above formula (I) and a pharmaceutically acceptable salt thereof to a patient suffering from arthropathy.

(27) The method for preventing or treating arthropathy according to the above (26) by administering an effective dose of at least one of the coumarin derivative and a pharmaceutical acceptable salt thereof, wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

(28) The method for preventing or treating arthropathy according to the above (27) by administering an effective dose of at least one of the coumarin derivative and a pharmaceutical acceptable salt thereof, wherein $R_1$ and $R_2$ are the same or different, and are phenyl substituted with alkoxy, alkyl, cyano, nitro, hydroxy, trifluoromethyl, amino, carboxy, alkoxycarbonyl, phenyl or one or two halogen(s).

(29) The method for preventing or treating arthropathy according to the above (28) by administering an effective dose of at least one of the coumarin derivative and a pharmaceutical acceptable salt thereof, wherein one of $R_1$ and $R_2$ is phenyl substituted with trifluoromethyl.

(30) The method for preventing or treating arthropathy according to the above (29) by administering an effective dose of at least one of the coumarin derivative and a pharmaceutical acceptable salt thereof, wherein $R_1$ or $R_2$ which is not phenyl substituted with trifluoromethyl is phenyl substituted with trifluoromethyl or halogen.

(31) The method for preventing or treating arthropathy according to the above (30) by administering an effective dose of at least one of the coumarin derivative and a pharmaceutical acceptable salt thereof, wherein the halogen is bromine.

(32) The method for preventing or treating arthropathy according to any of the above (26) to (31), wherein the arthropathy is osteoarthritis.

(33) The method for preventing or treating arthropathy according to any of the above (26) to (31), wherein the arthropathy is chronic rheumatoid arthritis.

(34) Use of the coumarin derivative represented by the above formula (I) or a pharmaceutically acceptable salt thereof in the manufacture of a pharmaceutical agent for the prevention or the therapy of arthropathy.

(35) The use of the coumarin derivative represented by the above formula (I) or a pharmaceutically acceptable salt thereof according to the above (34), wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

(36) The use of the coumarin derivative represented by the above formula (I) or a pharmaceutically acceptable salt thereof according to the above (35), wherein $R_1$ and $R_2$ are the same or different, and are phenyl substituted with alkoxy, alkyl, cyano, nitro, hydroxy, trifluoromethyl, amino, carboxy, alkoxycarbonyl, phenyl or one or two halogen(s).

(37) The use of the coumarin derivative represented by the above formula (I) or a pharmaceutically acceptable salt thereof according to the above (36), wherein one of $R_1$ and $R_2$ is phenyl substituted with trifluoromethyl.

(38) The use of the coumarin derivative represented by the above formula (I) or a pharmaceutically acceptable salt thereof according to the above (37), wherein $R_1$ or $R_2$ which is not phenyl substituted with trifluoromethyl is phenyl substituted with trifluoromethyl or halogen.

(39) The use of the coumarin derivative represented by the above formula (I) or a pharmaceutically acceptable salt thereof according to the above (38), wherein halogen is bromine.

(40) The use according to any of the above (34) to (39), wherein the arthropathy is osteoarthritis.

(41) The use according to any of the above (34) to (39), wherein the arthropathy is chronic rheumatoid arthritis.

The compound of the present invention may be made into a pharmaceutical composition in which various kinds of pharmaceutical additives such as excipient, binder, moisturizer, disintegrant, lubricant and diluent are combined therewith upon necessity depending upon the dosage form. As to an oral agent, it is possible to prepare a dosage form such as tablets, capsules, diluted powder, granules, liquid, syrup and sublingual agent. As to a parenteral agent, it is possible to prepare an injection preparation for hypodermic, intramuscular, intraarticular or intravenous administration as well as suppository for intrarectal administration and inhalant for intranasal administration. In the prescription, the compound of the present invention may be used in a form of a pharmaceutically acceptable salt thereof or may be used either solely or jointly in an appropriate combination. It is also possible to use as a combination drug with other pharmaceutically active ingredient.

With regard to the additive in preparing an oral agent, it is possible to appropriately combine commonly used excipient (such as lactose, mannitol, corn starch or potato starch), binder (such as crystalline cellulose, cellulose derivative, gum arabic, corn starch or gelatin), disintegrant (such as corn starch, potato starch or carboxymethyl cellulose potassium), lubricant (such as talc or magnesium stearate) and others (such as extender, moisturizer, buffer, preservative or fragrance) and it is also possible to add corrigent, aromatizing agent, etc. thereto.

When preparation is conducted as a liquid agent or as an emulsified, suspended or viscous injection agent, it is also possible to appropriately add commonly used solubilizing agent, suspending agent, emulsifier, stabilizer, preservative, isotonic agent, thickening agent, base for intraarticular administration, etc. and, usually, a sterilizing treatment is carried out.

Although the preferred dose of the compound of the present invention may vary depending upon the subject to be administered (age, body weight, etc. of a patient), type and extent of the disease, dosage form, administering method, administering period, etc., it is usual that 0.5 to 1000 mg or, preferably, 1 to 500 mg of the compound of the present invention is orally administered to an adult once daily or by dividing into several times a day. In the case of parenteral administration, the daily dose is made into a level of from one-third to one-tenth of each of the above-mentioned doses and, usually, it may be administered once daily or by dividing into several times a day. In the case of a sustained-release preparation where a drug is released for a very long period, it is preferred to administer about once a week to once a year.

EXAMPLES

The present invention will now be specifically illustrated hereunder by Examples but the present invention is not limited thereto at all.

Melting point was measured using a melting point measuring device of a Yamato MP-21 type and no correction was conducted for a thermometer. NMR spectrum was measured using a nuclear magnetic resonance device of a Brucker Avance III 500 type using tetramethylsilane as an internal standard. Silica gel column chromatography was conducted using PSQ 100 B (manufactured by Fuji Silysia Chemical). Thin layer chromatography was conducted using Silica Gel F254 (Merck No. 5715) and, for the detection, UV lamp was used together with a coloring reagent of a 5 w/v % ethanolic solution of phosphomolybdic acid and iodine-silica gel. With regard to reagents and solvents, the commercially available ones were used just they were.

Example 1

(1) Production of 3-acetylamino-2-oxochromen-8-yl benzenesulfonate

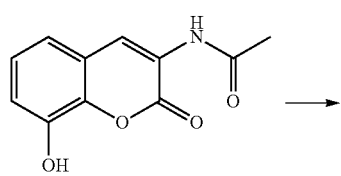

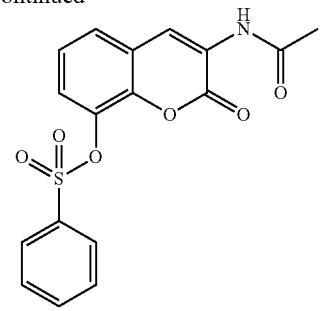

Benzenesulfonyl chloride (4.0 g, 22.8 mmol) was added to a solution of 3-acetylamino-2-oxo-8-hydroxychromen (5.0 g, 22.8 mmol) in pyridine (50 mL) followed by stirring for one night. Chloroform (100 mL) was added thereto and crystals were filtered therefrom and washed with hexane. The crystals were dried to give 7.0 g (85%) of the title compound.

Mp. 229-231° C. $^1$H-NMR (DMSO-$d_6$) δ: 2.15 (s, 3H), 7.22-7.34 (m, 2H), 7.58-7.89 (m, 6H), 8.58 (s, 1H), 9.81 (s, 1H).

(2) Production of 3-amino-2-oxochromen-8-yl benzenesulfonate

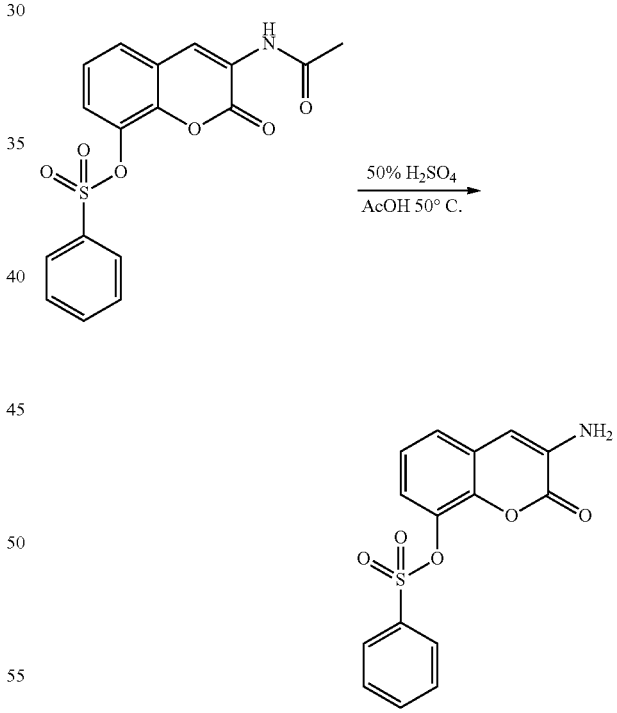

To a solution of the compound produced in the above (1) (3.0 g, 8.3 mmol) in acetic acid (30 mL) was added 50 vol % sulfuric acid (30 mL) followed by stirring at 50° C. After the crystals were completely dissolved, the reaction mixture was allowed to cool and added to water. The crystals separated out therefrom were filtered and dried to give 2.2 g (83%) of the title compound.

Mp. 129-131° C. $^1$HNMR (DMSO-$d_6$) δ: 5.88 (s, 2H), 6.64 (s, 1H), 6.93-7.87 (m, 8H).

(3) Production of 3-[(4-nitrophenyl)sulfonylamino]-2-oxochromen-8-yl benzenesulfonate [Compound 23]

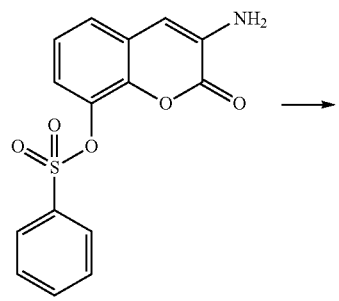

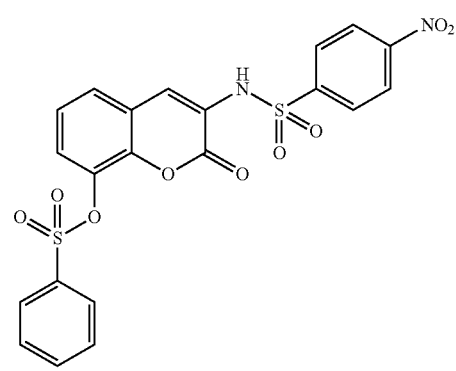

To a solution of the compound produced in the above (2) (1 g, 3.2 mmol) in pyridine (10 mL) was added 4-nitrobenzenesulfonyl chloride (1.0 g, 4.8 mmol) followed by stirring at room temperature for one night. After the solvent was evaporated therefrom in vacuo, the residue was purified by silica gel column chromatography (hexane:ethyl acetate=3:2 and then 100% chloroform). The resulting crude crystals were recrystallized from chloroform to give 0.8 g (52%) of the compound 23.

Example 2

Production of 3-[(4-methoxyphenyl)sulfonylamino]-2-oxochromen-8-yl 4-methoxybenzenesulfonate [Compound 1]

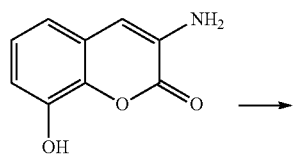

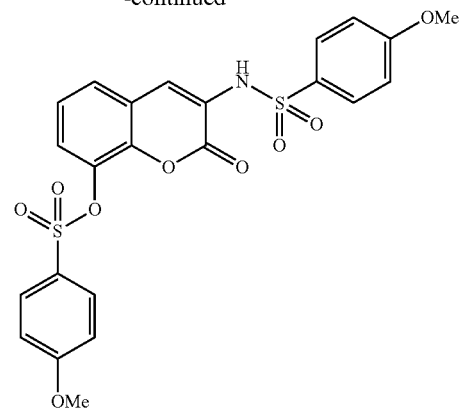

3-Amino-2-oxo-8-hydroxychromen (500 mg, 2.8 mmol) was suspended in methylene chloride (20 mL), pyridine (1.4 mL, 17 mmol) was dropped thereinto under cooling with ice, then 4-methoxybenzenesulfonyl chloride (3.5 g, 17 mmol) was added thereto under cooling with ice and the mixture was stirred at room temperature for 15 hours. The reaction solution was washed with water and a saturated saline solution and the organic layer was dried over sodium sulfate. The solvent was evaporated therefrom in vacuo and the resulting residue was purified by silica gel column chromatography (chloroform:methanol=120:1) to give 980 mg (67%) of the compound 1 as a solid.

Example 3

Production of 3-[(4-hydroxyphenyl)sulfonylamino]-2-oxochromen-8-yl 4-hydroxybenzenesulfonate [Compound 19]

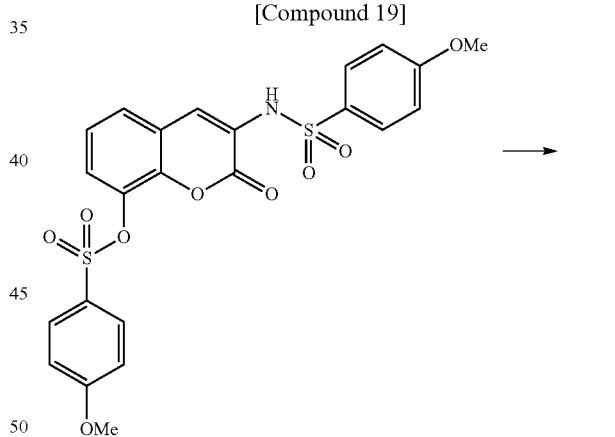

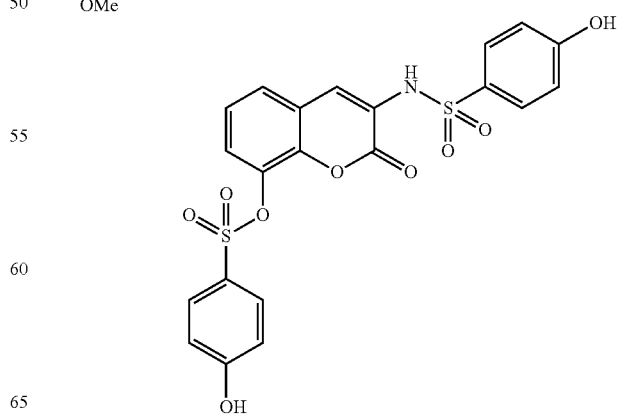

The compound 1 (300 mg, 0.6 mmol) was dissolved in anhydrous methylene chloride (1.8 mL), substitution with argon was conducted and the mixture was cooled down to −78° C. Boron tribromide (3.8 mL, 3.8 mmol) was dropped into the reaction solution followed by stirring at room temperature for 20 hours. Ice water was added to the reaction solution and the solid separated out therefrom were filtered and dried in vacuo over diphosphorus pentaoxide. This solid was purified by silica gel column chromatography (chloroform:methanol=95:5) to give 40 mg (14%) of the compound 19 as a solid.

Example 4

Production of 2-oxo-3-[[3-(trifluoromethyl)phenyl]-sulfonylamino]chromen-8-yl 4-aminobenzene-sulfonate [Compound 46]

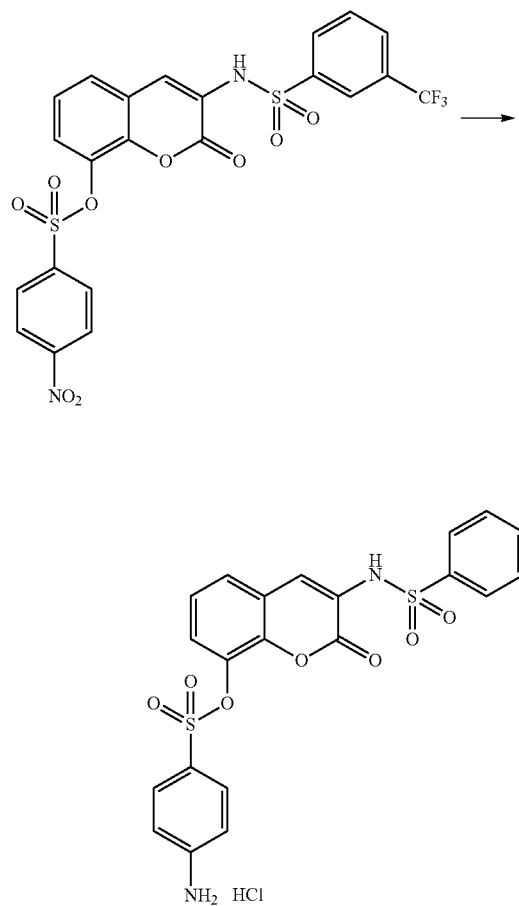

5% Pd—C (10 mg) was added to a solution of the compound 41 (0.2 g, 0.4 mmol) produced by the same method as in Example 1 in chloroform (10 mL) followed by stirring in a hydrogen atmosphere for 2 hours. After filtering off the catalyst, the solvent was evaporated therefrom in vacuo and a hydrogen chloride-dioxane solution (0.2 mL, 0.8 mmol) was added to the residue. The solvent was evaporated in vacuo and the crystals separated out therefrom were filtered and dried to give 30 mg (15%) of the compound 46.

Example 5

Production of 4-[3-[(3-nitrophenyl)sulfonylamino]-2-oxochromen-8-yl]oxysulfonylbenzoic acid [Compound 49]

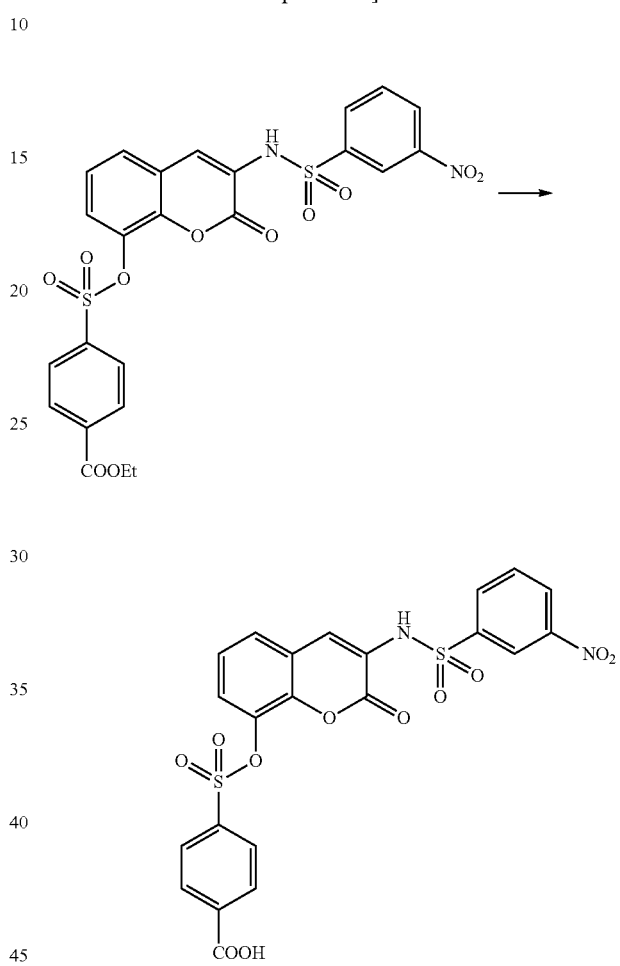

To a solution of the compound 48 (0.1 g, 0.2 mmol) produced by the same method as in Example 1 in methanol (5 mL) was added a 10 mol/L aqueous solution of sodium hydroxide (0.2 mL, 2 mmol as NaOH) followed by stirring at room temperature for 0.5 hour. The solvent was evaporated therefrom in vacuo, water (5 mL) was added to the residue and the mixture was extracted with chloroform. The solvent was evaporated in vacuo and the residue was crystallized from petroleum ether-ether to give 20 mg (22%) of the compound 49.

With regard to compounds other than the above-mentioned ones, they were produced using appropriate starting materials whereupon the compounds 2 to 18, 32 and 33 were produced by the same method as in Example 2, the compound 47 was produced by the same method as in Example 4 and other compounds were produced by the same method as in Example 1.

Physical property data of the compounds of the present invention produced in the above Examples are shown in Tables 3 to 9.

TABLE 3

| Compound No. | Physical Property |
|---|---|
| Compound 1 | Mp. 161-162° C. $^1$H-NMR (DMSO-$d_6$) δ: 3.82 (s, 3H), 3.83 (s 3H), 7.08-7.11 (m, 4H), 7.18-7.20 (m, 1H), 7.30-7.33 (m, 1H), 7.75-7.86 (m, 4H), 7.87-7.88 (m, 2H), 10.28 (s, 1H). |
| Compound 2 | Mp. 125-126° C. $^1$H-NMR (DMSO-$d_6$) δ: 3.78 (s, 3H), 3.82 (s, 3H), 7.25-7.34 (m, 6H), 7.42-7.52 (m, 4H), 7.73-7.75 (m, 1H), 7.81 (s, 1H), 10.46 (s, 1H). |
| Compound 3 | Mp. 130-131° C. $^1$H-NMR (DMSO-$d_6$) δ: 3.72 (s, 3H), 3.87 (s, 3H), 7.01-7.04 (m, 1H), 7.06-7.09 (m, 1H), 7.22-7.31 (m, 4H), 7.63-7.71 (m, 3H), 7.72-7.74 (m, 1H), 7.78-7.80 (m, 2H), 9.69 (s, 1H). |
| Compound 4 | Mp. 180-181° C. $^1$H-NMR (DMSO-$d_6$) δ: 2.36 (s, 3H), 2.37 (s, 3H), 7.19-7.21 (m, 1H), 7.30-7.33 (m, 1H), 7.39-7.41 (m, 4H), 7.70-7.72 (m, 3H), 7.77 (s, 1H), 7.81-7.83 (m, 2H), 10.37 (s, 1H). |
| Compound 5 | Mp. 125-126° C. $^1$H-NMR (DMSO-$d_6$) δ: 2.31 (s, 3H), 2.39 (s, 3H), 7.25-7.27 (m, 1H), 7.31-7.33 (m, 1H), 7.41-7.42 (m, 1H), 7.48-7.55 (m, 4H), 7.70-7.73 (m, 3H), 7.77-7.78 (m, 2H), 10.41 (s, 1H). |
| Compound 6 | Mp. 75-76° C. $^1$H-NMR (DMSO-$d_6$) δ: 2.62 (s, 3H), 2.72 (s, 3H), 7.20-7.50 (m, 6H), 7.55-7.65 (m, 4H), 7.66-7.87 (m, 2H), 10.55 (s, 1H). |
| Compound 7 | Mp. 200-201° C. $^1$H-NMR (DMSO-$d_6$) δ: 7.30-7.35 (m, 2H), 7.66-7.74 (m, 5H), 7.85-7.87 (m, 3H), 7.91-7.92 (m, 2H), 10.55 (s, 1H). |
| Compound 8 | Mp. 105-106° C. $^1$H-NMR (DMSO-$d_6$) δ: 7.36-7.37 (m, 2H), 7.58-7.65 (m, 2H), 7.76-7.81 (m, 4H), 7.86-7.89 (m, 3H), 7.98-7.99 (m, 1H), 10.60 (s, 1H). |
| Compound 9 | Mp. 180-181° C. $^1$H-NMR (DMSO-$d_6$) δ: 7.21-7.23 (m, 1H), 7.29-7.32 (m, 1H), 7.50-7.55 (m, 2H), 7.68-7.70 (m, 3H), 7.78-7.82 (m, 3H), 7.87-7.89 (m, 1H), 8.02-8.04 (m, 1H), 10.58 (s, 1H). |
| Compound 10 | Mp. 195-196° C. $^1$H-NMR (DMSO-$d_6$) δ: 7.29-7.35 (m, 2H), 7.41-7.45 (m, 4H), 7.74-7.75 (m, 1H), 7.83 (s, 1H), 7.90-7.93 (m, 2H), 7.96-7.99 (m, 2H), 10.46 (s, 1H). |

TABLE 4

| Compound No. | Physical Property |
|---|---|
| Compound 11 | Mp. 150-151° C. $^1$H-NMR (DMSO-$d_6$) δ: 7.32-7.38 (m, 2H), 7.56-7.69 (m, 5H), 7.75-7.78 (m, 4H), 7.86 (s, 1H), 10.58 (s, 1H). |
| Compound 12 | Mp. 200-201° C. $^1$H-NMR (DMSO-$d_6$) δ: 7.33-7.40 (m, 4H), 7.45-7.53 (m, 2H), 7.71-7.76 (m, 3H), 7.82-7.85 (m, 3H), 10.65 (s, 1H). |
| Compound 13 | Mp. 130-131° C. $^1$H-NMR (DMSO-$d_6$) δ: 7.25-7.45 (m, 2H), 7.76 (s, 1H), 7.87 (s, 1H), 7.95-8.20 (m, 8H), 10.74 (s, 1H). |
| Compound 14 | Mp. 205-206° C. $^1$H-NMR (DMSO-$d_6$) δ: 7.37 (s, 2H), 7.38-7.84 (m, 4H), 8.10-8.12 (m, 1H), 8.17-8.23 (m, 3H), 8.39 (s, 1H), 8.46 (s, 1H), 10.67 (s, 1H). |
| Compound 15 | Mp. 225-226° C. $^1$H-NMR (DMSO-$d_6$) δ: 7.36-7.39 (m, 1H), 7.42-7.44 (m, 1H), 7.72-7.74 (m, 1H), 7.85-7.95 (m, 5H), 7.97-7.99 (m, 1H), 8.05-8.06 (m, 1H), 8.09-8.10 (m, 1H), 8.18-8.20 (m, 1H), 10.85 (s, 1H). |
| Compound 16 | Mp. 230-231° C. $^1$H-NMR (DMSO-$d_6$) δ: 7.36-7.38 (m, 2H), 7.76-7.77 (m, 1H), 7.87-7.88 (m, 1H), 8.12-8.16 (m, 4H), 8.36-8.41 (m, 4H), 10.80 (s, 1H). |
| Compound 17 | Mp. 175-176° C. $^1$H-NMR (DMSO-$d_6$) δ: 7.36-7.39 (m, 1H), 7.43-7.45 (m, 1H), 7.77-7.79 (m, 1H), 7.83-7.86 (m, 1H), 7.88-7.91 (m, 2H), 8.20-8.22 (m, 1H), 8.29-8.31 (m, 1H), 8.49-8.52 (m, 3H), 8.65 (s, 1H), 10.75 (s, 1H). |
| Compound 18 | Mp. 180-181° C. $^1$H-NMR (DMSO-$d_6$) δ: 7.37-7.39 (m, 2H), 7.76 (s, 1H), 7.81-7.85 (m, 1H), 7.85-7.90 (m, 3H), 7.98-8.03 (m, 3H), 8.08-8.10 (m, 1H), 8.16-8.18 (m, 1H), 10.75 (s, 1H). |
| Compound 19 | Mp. 215-216° C. $^1$H-NMR (DMSO-$d_6$) δ: 6.86-7.13 (m, 6H), 7.38-7.40 (m, 1H), 7.67-7.68 (m, 1H), 7.71-7.77 (m, 4H), 10.17 (s, 1H), 10.38-10.56 (m, 2H). |

TABLE 4-continued

| Compound No. | Physical Property |
|---|---|
| Compound 20 | Mp. 227-228° C. $^1$H-NMR (DMSO-$d_6$) δ: 7.33-7.35 (m, 2H), 7.59-7.62 (m, 2H), 7.68-7.69 (m, 1H), 7.76-7.77 (m, 1H), 7.82 (s, 1H), 7.91-7.93 (m, 2H), 8.04-8.10 (m, 4H), 10.49 (s, 1H). |

TABLE 5

| Compound No. | Physical Property |
|---|---|
| Compound 21 | Mp. 89-90° C. $^1$H-NMR (DMSO-$d_6$) δ: 7.57-7.60 (m, 2H), 7.72-7.73 (m, 2H), 7.82-7.84 (m, 3H), 8.06-8.11 (m, 6H), 10.73 (s, 1H). |
| Compound 22 | Mp. 86-89° C. $^1$H-NMR (DMSO-$d_6$) δ: 7.59-7.61 (m, 2H), 7.74-7.76 (m, 2H), 7.78-7.80 (m, 3H), 8.12-8.16 (m, 6H), 10.69 (s, 1H). |
| Compound 23 | Mp. 154-155° C. $^1$H-NMR (DMSO-$d_6$) δ: 7.27-8.42 (m, 14H), 10.81 (brs, 1H). |
| Compound 24 | Mp. 116-117° C. $^1$H-NMR (DMSO-$d_6$) δ: 7.26-8.68 (m, 13H), 10.79 (brs, 1H). |
| Compound 25 | Mp. 130-132° C. $^1$H-NMR (DMSO-$d_6$) δ: 7.26-7.84 (m, 13H), 10.56 (brs, 1H). |
| Compound 26 | Mp. 157-159° C. $^1$H-NMR (DMSO-$d_6$) δ: 7.27-8.06 (m, 12H), 10.57 (brs, 1H). |
| Compound 27 | Mp. 173-175° C. $^1$H-NMR (DMSO-$d_6$) δ: 7.28-8.13 (m, 13H), 10.70 (brs, 1H). |
| Compound 28 | Mp. 157-159° C. $^1$H-NMR (DMSO-$d_6$) δ: 7.27-8.26 (m, 13H), 10.66 (brs, 1H). |
| Compound 29 | Mp. 140-142° C. $^1$H-NMR (DMSO-$d_6$) δ: 7.27-7.91 (m, 13H), 10.53 (brs, 1H). |
| Compound 30 | Mp. 166-168° C. $^1$H-NMR (DMSO-$d_6$) δ: 7.25-8.01 (m, 18H), 10.50 (brs, 1H). |
| Compound 31 | Mp. 165-167° C. $^1$H-NMR (DMSO-$d_6$) δ: 7.28-8.11 (m, 13H), 10.57 (brs, 1H). |
| Compound 32 | Mp. 139-140° C. $^1$H-NMR (DMSO-$d_6$) δ: 7.35-8.12 (m, 12H), 10.61 (brs, 1H). |
| Compound 33 | Mp. 136-138° C. $^1$H-NMR (DMSO-$d_6$) δ: 7.37-8.26 (m, 12H), 10.67 (brs, 1H). |
| Compound 34 | Mp. 121-124° C. $^1$H-NMR (DMSO-$d_6$) δ: 7.32-7.98 (m, 13H), 10.49 (brs, 1H). |
| Compound 35 | Mp. 127-129° C. $^1$H-NMR (DMSO-$d_6$) δ: 7.35-8.12 (m, 13H), 10.47 (brs, 1H). |
| Compound 36 | Mp. 149-151° C. $^1$H-NMR (DMSO-$d_6$) δ: 7.37-8.97 (m, 12H), 10.59 (brs, 1H). |

TABLE 6

| Compound No. | Physical Property |
|---|---|
| Compound 37 | Mp. 151-153° C. $^1$H-NMR (DMSO-$d_6$) δ: 3.49 (s, 3H), 7.38-8.16 (m, 8H), 10.64 (brs, 1H). |
| Compound 38 | Mp. 181-183° C. $^1$H-NMR (DMSO-$d_6$) δ: 7.35-9.06 (m, 11H), 10.70 (brs, 1H). |
| Compound 39 | Mp. 150-152° C. $^1$H-NMR (DMSO-$d_6$) δ: 3.17 (s, 3H), 7.33-8.05 (m, 8H), 9.74 (brs, 1H). |
| Compound 40 | Mp. 161-163° C. $^1$H-NMR (DMSO-$d_6$) δ: 3.16 (s, 3H), 7.25-7.90 (m, 9H), 9.70 (s, 1H). |
| Compound 41 | Mp. 186-188° C. $^1$H-NMR (DMSO-$d_6$) δ: 7.35-8.41 (m, 12H), 10.65 (brs, 1H). |
| Compound 42 | Mp. 101-103° C. $^1$H-NMR (DMSO-$d_6$) δ: 7.37-8.42 (m, 12H), 10.81 (brs, 1H). |
| Compound 43 | Mp. 155-157° C. $^1$H-NMR (DMSO-$d_6$) δ: 7.16-8.69 (m, 11H), 10.82 (brs, 1H). |
| Compound 44 | Mp. 138-141° C. $^1$H-NMR (DMSO-$d_6$) δ: 7.18-8.57 (m, 11H), 10.64 (brs, 1H). |
| Compound 45 | Mp. 127° C. (dec.). $^1$H-NMR (DMSO-$d_6$) δ: 7.39-8.67 (m, 12H), 9.76 (brs, 1H). |
| Compound 46 | Mp. 114° C. (dec.). $^1$H-NMR (DMSO-$d_6$) δ: 6.57-8.27 (m, 15H), 10.67 (brs, 1H). |
| Compound 47 | Mp. 136-138° C. $^1$H-NMR (DMSO-$d_6$) δ: 6.12 (brs, 2H), 6.57-8.13 (m, 12H), 9.92 (s, 1H). |

TABLE 6-continued

| Compound No. | Physical Property |
|---|---|
| Compound 48 | Mp. 153-154° C. $^1$H-NMR (DMSO-$d_6$) δ: 1.34 (t, J = 6.5 Hz, 3H), 4.36 (q, J = 6.5 Hz, 2H), 7.25-8.68 (m, 12H), 10.79 (brs, 1H). |
| Compound 49 | Mp. 168-170° C. $^1$H-NMR (DMSO-$d_6$) δ: 7.24-7.35 (m, 2H), 7.79-8.71 (m, 10H), 10.79 (brs, 1H). |
| Compound 50 | Mp. 166-167° C. $^1$H NMR (DMSO-$d_6$) δ: 7.39 (dd, J = 8.0, 8.0 Hz, 1 H), 7.43-7.45 (m, 1 H), 7.80 (dd, J = 8.0, 1.5 Hz, 1 H), 7.83-7.87 (m, 2 H), 7.90 (s, 1 H), 8.10 (d, J = 8.0 Hz, 1 H), 8.19 (d, J = 8.0 Hz, 1 H), 8.21-8.23 (m, 1 H), 8.25 (s, 1 H), 8.51-8.55 (m, 2 H), 10.65 (brs, 1 H). |

TABLE 7

| Compound No. | Physical Property |
|---|---|
| Compound 51 | Mp. 170-171° C. $^1$H NMR (DMSO-$d_6$) δ: 7.36-7.42 (m, 2 H), 7.77-7.78 (m, 1 H), 7.83 (dd, J = 8.0, 8.0 Hz, 1 H), 7.87-7.91 (m, 2 H), 8.02 (s, 1 H), 8.10 (d, J = 8.0 Hz, 1 H), 8.14 (d, J = 8.0 Hz, 1 H), 8.31-8.33 (m, 1 H), 8.51-8.53 (m, 1 H), 8.68-8.69 (m, 1 H), 10.79 (brs, 1 H). |
| Compound 52 | Mp. 153-154° C. $^1$H NMR (DMSO-$d_6$) δ: 7.36-7.40 (m, 2 H), 7.44 (dd, J = 7.4, 7.4 Hz, 1 H), 7.50 (dd, J = 7.7, 7.7 Hz, 1 H), 7.75 (d, J = 7.5 Hz, 2 H), 7.78-7.83 (m, 2 H), 7.85 (s, 1 H), 7.90-7.92 (m, 2 H), 8.00-8.02 (m, 2 H), 8.05-8.07 (m, 2 H), 8.13 (d, J = 8.0 Hz, 1 H), 10.51 (brs, 1 H) |
| Compound 53 | Mp. 146-147° C. $^1$H NMR (DMSO-$d_6$) δ: 7.32-7.38 (m, 2 H), 7.43-7.46 (m, 1 H), 7.48-7.52 (m, 3 H), 7.74-7.81 (m, 4 H), 7.86-7.92 (m, 4 H), 7.96 (dd, J = 6.9, 6.9 Hz, 1 H), 8.01 (d, J = 8.6 Hz, 2 H), 10.54 (brs, 1 H). |
| Compound 54 | Mp. 172-173° C. $^1$H NMR (DMSO-$d_6$) δ: 7.49 (dd, J = 8.0, 8.0 Hz, 1 H), 7.54-7.56 (m, 1 H), 7.68 (dd, J = 8.0, 8.0 Hz, 1 H), 7.80-7.83 (m, 1 H), 7.86-7.89 (m, 2 H), 7.91-7.95 (m, 2 H), 8.12 (m, 1 H), 8.23-8.25 (m, 1 H), 8.55-8.59 (m, 2 H), 10.59 (brs, 1 H) |
| Compound 55 | Mp. 204-205° C. $^1$H NMR (DMSO-$d_6$) δ: 7.37 (dd, J = 8.0, 8.0 Hz, 1 H), 7.41-7.46 (m, 2 H), 7.50-7.53 (m, 2 H), 7.76-7.84 (m, 5 H), 7.90-7.92 (m, 2 H), 7.98-8.00 (m, 2 H), 8.17-8.20 (m, 1 H), 8.46-8.48 (m, 1 H), 8.55-8.56 (m, 1 H), 10.51 (brs, 1 H). |
| Compound 56 | Mp. 158-159° C. $^1$H NMR (DMSO-$d_6$) δ: 7.36-7.44 (m, 2 H), 7.55 (dd, J = 8.0, 8.0 Hz, 1 H), 7.77-7.79 (m, 1 H), 7.82-7.85 (m, 2 H), 7.90-7.93 (m, 2 H), 8.04 (s, 1 H), 8.09-8.11 (m, 2 H), 8.13 (d, J = 8.0 Hz, 1 H), 10.57 (brs, 1 H) |
| Compound 57 | Mp. 140-141° C. $^1$H NMR (DMSO-$d_6$) δ: 7.35-7.39 (m, 2 H), 7.78 (dd, J = 6.6, 2.8 Hz, 1 H), 7.85 (dd, J = 7.9, 7.9 Hz, 1 H), 7.89 (s, 1 H), 7.98 (d, J = 8.4 Hz, 1 H), 8.07-8.10 (m, 3 H), 8.21 (d, J = 8.0 Hz, 1 H), 8.25 (s, 1 H), 10.66 (brs, 1 H). |

TABLE 8

| Compound No. | Physical Property |
|---|---|
| Compound 58 | Mp. 151-152° C. $^1$H NMR (DMSO-$d_6$) δ: 7.33-7.39 (m, 2 H), 7.54 (dd, J = 8.0, 8.0 Hz, 1 H), 7.78 (dd, J = 7.4, 2.0 Hz, 1 H), 7.84 (s, 1 H), 7.89-7.93 (m, 2 H), 8.00 (d, J = 8.4 Hz, 2 H), 8.10-8.12 (m, 3 H), 10.58 (brs, 1 H). |
| Compound 59 | Mp. 163-164° C. $^1$H NMR (DMSO-$d_6$) δ: 7.35-7.40 (m, 2 H), 7.53 (dd, J = 8.0, 8.0 Hz, 1 H), 7.78 (dd, J = 7.1, 2.3 Hz, 1 H), 7.81-7.83 (m, 1 H), 7.90-7.95 (m, 3 H), 7.97 (dd, J = 1.9, 1.9 Hz, 1 H), 8.33-8.35 (m, 1 H), 8.52-8.54 (m, 1 H), 8.70 (dd, J = 1.9, 1.9 Hz, 1 H), 10.83 (brs, 1 H). |
| Compound 60 | Mp. 135-136° C. $^1$H NMR (DMSO-$d_6$) δ: 7.35-7.40 (m, 2 H), 7.52 (dd, J = 8.0, 8.0 Hz, 1 H), 7.79 (dd, J = 7.3, 2.1 Hz, 1 H), 7.81-7.83 (m, 1 H), 7.86 (dd, J = 7.9, 7.9 Hz, 1 H), 7.91-7.93 (m, 2 H), 7.96 (dd, J = 1.8, 1.8 Hz, 1 H), 8.10 (d, J = 7.8 Hz, 1 H), 8.22 (d, J = 8.1 Hz, 1 H), 8.27 (s, 1 H), 10.69 (brs, 1 H). |

TABLE 8-continued

| Compound No. | Physical Property |
|---|---|
| Compound 61 | Mp. 176-177° C. $^1$H NMR (DMSO-$d_6$) δ: 7.40-7.45 (m, 2 H), 7.58 (dd, J = 8.0, 8.0 Hz, 1 H), 7.83 (dd, J = 6.6, 2.6 Hz, 1 H), 7.87 (d, J = 8.0 Hz, 1 H), 7.95-7.98 (m, 2 H), 8.02 (s, 1 H), 8.06 (d, J = 8.4 Hz, 2 H), 8.19 (d, J = 8.2 Hz, 2 H), 10.79 (brs, 1 H). |
| Compound 62 | Mp. 192-193° C. $^1$H NMR (DMSO-$d_6$) δ: 7.30-7.38 (m, 2 H), 7.47-7.55 (m, 3 H), 7.70-7.72 (m, 2 H), 7.75 (dd, J = 7.8, 1.5 Hz, 1 H), 7.83 (dd, J = 8.0, 8.0 Hz, 1 H), 7.88-7.94 (m, 5 H), 8.29-8.31 (m, 1 H), 8.43-8.46 (m, 1 H), 8.66 (dd, J = 1.9, 1.9 Hz, 1 H), 10.90 (brs, 1 H). |
| Compound 63 | Mp. 170-171° C. $^1$H NMR (DMSO-$d_6$) δ: 7.37 (dd, J = 8.2, 1.6 Hz, 1 H), 7.42 (dd, J = 8.0, 8.0 Hz, 1 H), 7.53-7.61 (m, 3 H), 7.76-7.78 (m, 2 H), 7.81-7.85 (m, 2 H), 7.95-8.00 (m, 5 H), 8.08 (d, J = 7.9 Hz, 1 H), 8.24 (d, J = 8.0 Hz, 1 H), 8.30 (s, 1 H), 10.71 (brs, 1 H) |
| Compound 64 | Mp. 196-197° C. $^1$H NMR (DMSO-$d_6$) δ: 7.29-7.36 (m, 2 H), 7.46-7.54 (m, 3 H), 7.69-7.74 (m, 3 H), 7.83-7.92 (m, 7 H), 8.08 (d, J = 8.2 Hz, 2 H), 10.70 (brs, 1 H) |

TABLE 9

| Compound No. | Physical Property |
|---|---|
| Compound 65 | Mp. 182-183° C. $^1$H NMR (DMSO-$d_6$) δ: 7.31-7.38 (m, 2 H), 7.47-7.56 (m, 4 H), 7.71-7.73 (m, 2 H), 7.77 (dd, J = 7.8, 1.5 Hz, 1 H), 7.83-7.96 (m, 7 H), 8.10 (dd, J = 1.8, 1.8 Hz, 1 H), 10.57 (brs, 1 H) |
| Compound 66 | Mp. 172-173° C. $^1$H NMR (DMSO-$d_6$) δ: 7.29 (dd, J = 8.2, 1.5 Hz, 1 H), 7.35 (dd, J = 8.0, 8.0 Hz, 1 H), 7.42-7.53 (m, 6 H), 7.68-7.71 (m, 4 H), 7.75 (dd, J = 7.9, 1.3 Hz, 1 H), 7.80-7.83 (m, 3 H), 7.86-7.88 (m, 2 H), 7.90-7.92 (m, 2 H), 7.96-7.98 (m, 2 H), 10.51 (brs, 1 H) |
| Compound 67 | Mp. 158-159° C. $^1$H NMR (DMSO-$d_6$) δ: 7.38 (dd, J = 8.0, 8.0 Hz, 1 H), 7.43-7.45 (m, 1 H), 7.78-7.79 (m, 1 H), 7.84-7.87 (m, 2 H), 8.01 (d, J = 8.0 Hz, 1 H), 8.11 (d, J = 8.0 Hz, 1 H), 8.21-8.23 (m, 1 H), 8.50-8.52 (m, 2 H), 8.55 (m, 1 H), 10.70 (brs, 1 H) |
| Compound 68 | Mp. 147-148° C. $^1$H NMR (DMSO-$d_6$) δ: 7.39 (dd, J = 8.0, 8.0 Hz, 1 H), 7.43-7.45 (m, 1 H), 7.78-7.79 (m, 1 H), 7.84 (dd, J = 8.0, 8.0 Hz, 1 H), 7.88 (s, 1 H), 8.00-8.02 (m, 3 H), 8.07 (d, J = 8.0 Hz, 1 H), 8.12-8.16 (m, 3 H), 10.71 (brs, 1 H) |
| Compound 69 | Mp. 165-166° C. $^1$H NMR (DMSO-$d_6$, 500 MHz) δ: 7.34-7.39 (m, 2 H), 7.78 (dd, J = 7.0, 2.5 Hz, 1 H), 7.88-7.91 (m, 2 H), 7.98 (d, J = 8.4 Hz, 2 H), 8.10 (d, J = 8.3 Hz, 2 H), 8.33-8.35 (m, 1 H), 8.50-8.52 (m, 1 H), 8.70 (dd, J = 2.0, 2.0 Hz, 1 H), 10.80 (brs, 1 H) |
| Compound 70 | Mp. 154-155° C. $^1$H NMR (DMSO-$d_6$) δ: 7.31-7.38 (m, 2 H), 7.42-7.46 (m, 1 H), 7.49-7.52 (m, 2 H), 7.73-7.75 (m, 2 H), 7.78 (dd, J = 7.7, 1.5 Hz, 1 H), 7.84 (s, 1 H), 7.89-7.90 (m, 2 H), 7.98-8.03 (m, 4 H), 8.11 (d, J = 8.0 Hz, 2 H), 10.53 (brs, 1 H) |

Test Example 1

Evaluation of Suppressive Action to Cartilage Destruction [Release of sGAG Induced by Interleukin-1α (IL-1α)]

(1) Incubation of Cartilage Pieces

Each four cartilage pieces of bovine metacarpophalangeal joint were placed in each well of a 48-well plate and pretreated for 2 hours with a basal medium [D-MEM (Dulbecco's Modified Eagle Medium) containing 2 mmol/L of glutamine, 25 mmol/L of Hepes, 100 μg/mL of streptomycin, 100 IU/mL of penicillin and 5.6 μg/mL of amphotericin B] containing 25 μmol/L of a test substance. Human recombinant IL-1α (3 ng/mL) was added thereto followed by incubating at 37° C. for 4 days in a $CO_2$ incubator set at 5 vol % of CO$_2$. Culture supernatant and cartilage pieces were recovered and stored by freezing until the measurement for each of them.

(2) Measurement of the Amount of sGAG and Calculation of the Suppressive Rate for the Release of sGAG The recovered cartilage pieces were treated with a papain solution [containing 1 mg/mL of papain, 100 mmol/L of sodium phosphate (pH 6.5), 5 mmol/L of L-cysteine and 5 mmol/L of disodium ethylenediaminetetraacetate (EDTA)] at 65° C. for about 16 hours to solubilize. Amount of sGAG in the resulting extract was measured using an sGAG Alcian Blue Binding Kit (Wieslab AB) which is a quantitative kit to which a Alcian blue staining protocol is applied. sGAG in the culture supernatant after the incubation was measured without subjecting to a papain treatment. Each releasing rate of sGAG was determined by the following formula to calculate the suppressive rate for the release of sGAG.

Releasing rate (%) of sGAG={(Total sGAG amount in the culture supernatant)/[(Total sGAG amount in the culture supernatant)+(Total sGAG amount in the cartilage pieces)]}×100

Suppressive rate (%) for release of sGAG={[Releasing rate of sGAG (IL-1α stimulation)−Releasing rate of sGAG (Test substance)]/[Releasing rate of sGAG (IL-1α stimulation)−Releasing rate of sGAG (Non-stimulation)]}×100

An example of the results is shown in Table 10. It has been confirmed that the compound of the present invention suppresses the release of sGAG induced by IL-1α and exhibits a suppressive action for cartilage destruction.

TABLE 10

| Test Substance | sGAG Releasing Suppressive Rate (%) |
|---|---|
| Compound 1 | 93 |
| Compound 13 | 44 |
| Compound 14 | 66 |
| Compound 16 | 112 |
| Compound 17 | 156 |
| Compound 18 | 81 |
| Compound 20 | 35 |
| Compound 21 | 69 |
| Compound 22 | 92 |
| Compound 23 | 103 |
| Compound 24 | 90 |
| Compound 25 | 77 |
| Compound 26 | 97 |
| Compound 27 | 162 |
| Compound 28 | 140 |
| Compound 29 | 121 |
| Compound 30 | 141 |
| Compound 31 | 135 |
| Compound 32 | 202 |
| Compound 33 | 147 |
| Compound 34 | 109 |
| Compound 35 | 103 |
| Compound 36 | 30 |
| Compound 37 | 17 |
| Compound 38 | 67 |
| Compound 41 | 172 |
| Compound 42 | 163 |
| Compound 43 | 107 |
| Compound 44 | 118 |
| Compound 46 | 98 |
| Compound 47 | 69 |
| Compound 48 | 122 |
| Compound 49 | 38 |
| Compound 50 | 163 |
| Compound 51 | 141 |
| Compound 52 | 126 |
| Compound 53 | 131 |
| Compound 54 | 136 |

TABLE 10-continued

| Test Substance | sGAG Releasing Suppressive Rate (%) |
|---|---|
| Compound 55 | 117 |
| Compound 56 | 133 |
| Compound 57 | 140 |
| Compound 58 | 129 |
| Compound 59 | 123 |
| Compound 60 | 138 |
| Compound 61 | 140 |
| Compound 62 | 140 |
| Compound 63 | 137 |
| Compound 64 | 136 |
| Compound 65 | 115 |
| Compound 66 | 38 |
| Compound 67 | 115 |
| Compound 68 | 124 |
| Compound 69 | 126 |
| Compound 70 | 103 |

Test Example 2

Evaluation of Suppressive Action to Cell Proliferation of Synovial Cells (HFLS-OA) Derived from Tissues of Human Osteoarthritis (1) Incubation of HFLS-OA Cells HFLS-OA cells were sown onto a 96-well plate so as to make them 10$^4$ cells/well/100 μL in a D-MEM containing 2 vol % of fetal bovine serum (FBS) and incubated for 24 hours. A test substance (200 μmol/L) and human recombinant TNF-α (10 ng/mL) were added thereto followed by incubating for 5 days.

(2) Measurement of Action to HFLS-OA Cell Proliferation

A kit [Cell Proliferation ELISA, BrdU (colorimetric) (Roche Diagnostics)] was used and measurement was conducted according to the protocol attached to the kit. HFLS-OA cells were incubated for 3 days and 10 μL of 5-bromo-2'-deoxyuridine (BrdU) dissolved in a phosphate buffered saline (PBS) (100 μmol/L, pH 7.4) was added to each well followed by incubating for 48 hours more. After the culture supernatant was removed from each well, 200 μL/well of an immobilization/denaturation solution was added thereto and the mixture was allowed to stand for 30 minutes whereby immobilization of the cells and denaturation of DNA were conducted. After the immobilization/denaturation solution was completely removed, 100 μL of a peroxidase-labeled anti-BrdU antibody solution was added thereto and the mixture was made to react at room temperature for 90 minutes. After washing with PBS, 100 μL of a substrate liquid (tetramethylbenzidine) was added to each well and the absorbance was measured. A cell proliferation rate upon addition of each test substance was calculated where an increase in incorporation of BrdU upon addition of TNF-α was defined as 100% of cell proliferation rate.

An example of the results is shown in Table 11. The compound of the present invention showed a strong suppressive action to the proliferation of HFLS-OA cells induced by TNF-α. In the meanwhile, a cytotoxicity test where a lactate dehydrogenase leaked out into a cell culture supernatant was used an indicator was also carried out but the above-mentioned suppressive action to the proliferation of synovial cells was not due to the cytotoxicity by the compound of the present invention.

TABLE 11

| Test Substance | Synovial Cell Proliferation Rate (%) |
|---|---|
| Compound 1 | −39.1 |
| Compound 2 | −52.2 |
| Compound 3 | −65.1 |
| Compound 4 | −88.1 |
| Compound 5 | −84.9 |
| Compound 6 | −77.4 |
| Compound 7 | −92.5 |
| Compound 8 | −94.4 |
| Compound 9 | −88.8 |
| Compound 10 | −34.9 |
| Compound 11 | −90.6 |
| Compound 12 | −91.8 |
| Compound 13 | −54.1 |
| Compound 14 | −60.3 |
| Compound 15 | −3.3 |
| Compound 16 | −19.9 |
| Compound 17 | −24.9 |
| Compound 18 | −23.8 |
| Compound 20 | −42.1 |
| Compound 21 | −41.2 |
| Compound 22 | −38.4 |
| Compound 23 | −39.0 |
| Compound 24 | −40.0 |
| Compound 25 | −40.9 |
| Compound 26 | −38.4 |
| Compound 27 | −36.3 |
| Compound 28 | −33.7 |
| Compound 29 | −31.3 |
| Compound 30 | −33.0 |
| Compound 31 | −37.1 |
| Compound 32 | −41.1 |
| Compound 33 | −40.0 |
| Compound 34 | −31.6 |
| Compound 35 | −31.5 |
| Compound 36 | −33.9 |
| Compound 37 | −22.6 |
| Compound 38 | −31.2 |
| Compound 39 | −43.0 |
| Compound 40 | −40.5 |
| Compound 41 | −37.7 |
| Compound 42 | −35.5 |
| Compound 43 | −30.3 |
| Compound 44 | −31.5 |
| Compound 45 | −37.0 |
| Compound 46 | −37.0 |
| Compound 47 | −40.1 |
| Compound 48 | −34.9 |
| Compound 49 | −36.1 |
| Compound 50 | −46.4 |
| Compound 51 | −36.5 |
| Compound 52 | −35.5 |
| Compound 53 | −32.3 |
| Compound 54 | −44.4 |
| Compound 55 | −32.2 |
| Compound 56 | −44.4 |
| Compound 57 | −50.0 |
| Compound 58 | −42.8 |
| Compound 59 | −32.8 |
| Compound 60 | −44.4 |
| Compound 61 | −40.6 |
| Compound 62 | −49.2 |
| Compound 63 | −47.9 |
| Compound 64 | −45.9 |
| Compound 65 | −45.9 |
| Compound 66 | −37.9 |
| Compound 67 | −38.9 |
| Compound 68 | −42.8 |
| Compound 69 | −40.6 |
| Compound 70 | −39.0 |

INDUSTRIAL APPLICABILITY

As shown in Table 10, the coumarin derivative according to the present invention showed an excellent suppressive action to the release of sGAG and suppressed the cartilage destruction in a pharmacological test where the release of sGAG of incubated cartilage cells to which 1L-1α, which is a cartilage destruction factor, was added was used as an indicator. Further, as shown in Table 11, the coumarin derivative according to the present invention showed an excellent suppressive action to the proliferation of synovial cells in a pharmacological test for the proliferation of incubated cartilage cells to which TNF-α inducing the proliferation of synovial cells was added. Accordingly, the compound of the present invention is highly useful as an active ingredient of a pharmaceutical composition which is a preventive or therapeutic agent for arthropathy such as osteoarthritis or chronic rheumatoid arthritis.

The invention claimed is:

1. A coumarin derivative represented by the following formula (I) or a pharmaceutically acceptable salt or hydrate thereof;

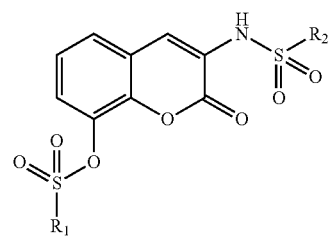

in the formula, $R_1$ and $R_2$ are the same or different, and are (a) phenyl optionally substituted with alkoxy, alkyl, cyano, nitro, hydroxy, trifluoromethyl, amino, carboxy, alkoxycarbonyl, phenyl or one or two halogen(s), (b) pyridyl, (c) alkyl or (d) thienyl.

2. The coumarin derivative or a pharmaceutically acceptable salt or hydrate thereof according to claim 1, wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

3. The coumarin derivative or a pharmaceutically acceptable salt or hydrate thereof according to claim 2, wherein $R_1$ and $R_2$ are the same or different, and are phenyl substituted with alkoxy, alkyl, cyano, nitro, hydroxy, trifluoromethyl, amino, carboxy, alkoxycarbonyl, phenyl or one or two halogen(s).

4. The coumarin derivative or a pharmaceutically acceptable salt or hydrate thereof according to claim 3, wherein both of $R_1$ and $R_2$ are phenyl substituted with trifluoromethyl.

5. The coumarin derivative or a pharmaceutically acceptable salt or hydrate thereof according to claim 3, wherein one of $R_1$ and $R_2$ is phenyl substituted with trifluoromethyl.

6. The coumarin derivative or a pharmaceutically acceptable salt or hydrate thereof according to claim 5, wherein one of $R_1$ and $R_2$ is phenyl substituted with trifluoromethyl, the other is phenyl substituted with halogen.

7. The coumarin derivative or a pharmaceutically acceptable salt or hydrate thereof according to claim 6, wherein the halogen is bromine.

8. A pharmaceutical agent containing at least one member of a coumarin derivative represented by the following formula (I) and a pharmaceutically acceptable salt and hydrate thereof;

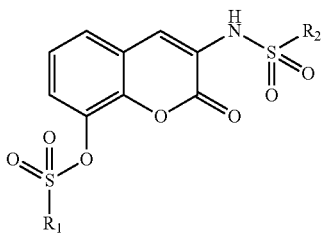

(I)

in the formula, $R_1$ and $R_2$ are the same or different, and are
(a) phenyl optionally substituted with alkoxy, alkyl, cyano, nitro, hydroxy, trifluoromethyl, amino, carboxy, alkoxycarbonyl, phenyl or one or two halogen(s), (b) pyridyl, (c) alkyl or (d) thienyl.

9. The pharmaceutical agent according to claim 8, wherein $R_1$ and $R_2$ are the same or different, and are phenyl optionally substituted with alkoxy, alkyl, cyano, nitro, hydroxy, trifluoromethyl, amino, carboxy, alkoxycarbonyl, phenyl or one or two halogen(s).

10. The pharmaceutical agent according to claim 9, wherein $R_1$ and $R_2$ are the same or different, and are phenyl substituted with alkoxy, alkyl, cyano, nitro, hydroxy, trifluoromethyl, amino, carboxy, alkoxycarbonyl, phenyl, or phenyl substituted with one or two halogen(s).

11. The pharmaceutical agent according to claim 10, wherein both of $R_1$ and $R_2$ are phenyl substituted with trifluoromethyl.

12. The pharmaceutical agent according to claim 10, wherein one of $R_1$ and $R_2$ is phenyl substituted with trifluoromethyl.

13. The pharmaceutical agent according to claim 12, wherein one of $R_1$ and $R_2$ is phenyl substituted with trifluoromethyl, the other is phenyl substituted with halogen.

14. The pharmaceutical agent according to claim 13, wherein the halogen is bromine.

15. The pharmaceutical agent according to claim 8, wherein the pharmaceutical agent is a therapeutic agent for arthropathy.

16. The pharmaceutical agent according to claim 15, wherein the arthropathy is osteoarthritis.

17. The pharmaceutical agent according to claim 15, wherein the arthropathy is chronic rheumatoid arthritis.

18. The pharmaceutical agent according to claim 8, wherein the pharmaceutical agent is an oral agent.

19. The pharmaceutical agent according to claim 8, wherein the pharmaceutical agent is an injection agent.

* * * * *